United States Patent [19]

Felcht

[11] 4,263,231
[45] Apr. 21, 1981

[54] PROCESS FOR THE MANUFACTURE OF 3-ACYL-2-ALKYL- AND 3-ACYL-2-ARYL-1,3,2-BENZOXAZAPHOSPHOLANES

[75] Inventor: Utz-Hellmuth Felcht, Bruchmühlbach, Fed. Rep. of Germany

[73] Assignee: Hoechst Aktiengesellschaft, Frankfurt am Main, Fed. Rep. of Germany

[21] Appl. No.: 49,298

[22] Filed: Jun. 18, 1979

[30] Foreign Application Priority Data

Jun. 19, 1978 [DE] Fed. Rep. of Germany ....... 2826622

[51] Int. Cl.³ .............................................. C07F 9/24
[52] U.S. Cl. .................................... 260/968; 260/936
[58] Field of Search ........................ 268/936; 260/968

[56] References Cited

U.S. PATENT DOCUMENTS 3,732,340   5/1973   Arnold et al. .................... 260/936

FOREIGN PATENT DOCUMENTS 46-18755   5/1971   Japan ....................... 260/936

447408 12/1975 U.S.S.R. ............................ 260/936

OTHER PUBLICATIONS

M. A. Pudovik et al., "J. Org. Chem. (USSR)", vol. 44, pp. 983–988, (1974) (English translation of Zh. Obsh. Khim. 44, 1020 (1974).
Pudovik et al., "Chem. Abs.", vol. 81, No. 11, (1974), No. 63723f.
Pudovik et al., "Chem. Abs.", vol. 79, No. 11, (1973), No. 66261y.

Primary Examiner—Anton H. Sutto
Attorney, Agent, or Firm—Curtis, Morris & Safford

[57] ABSTRACT

3-Acyl-2-alkyl- and 3-acyl-2-aryl-1,3,2-benzoxazaphospholanes are prepared by reacting dichlorophosphanes, 2-N-acylaminophenols and organic nitrogen bases binding hydrogen chloride in a molar proportion of about 1:1≧2 in an inert solvent in a one stage process without isolation of an intermediate product. The compounds obtained are, for the most part, novel and are used for the manufacture of alkyl- and aryl-1-oxophospholanes, which are used as catalysts for the production of rigid polyurethane foams.

9 Claims, No Drawings

PROCESS FOR THE MANUFACTURE OF 3-ACYL-2-ALKYL- AND 3-ACYL-2-ARYL-1,3,2-BENZOXAZAPHOSPHOLANES

3-Acyl-2-alkyl- and 3-acyl-2-aryl-1,3,2-benzoxazaphospholanes are compounds of the formula

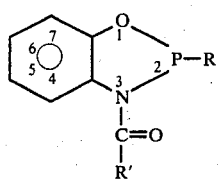

in which the radicals R and R', which may be identical or different, are organic radicals and the benzene nucleus may be substituted.

Compounds of this type are valuable intermediates for the manufacture of alkyl- and aryl-1-oxophospholenes (cf. M. and A. Pudovik, IZvt.Akad.Nauk. SSR, Ser.Khim. 964 (1975)). The synthesis of the oxophospholenes can be represented by the following equation:

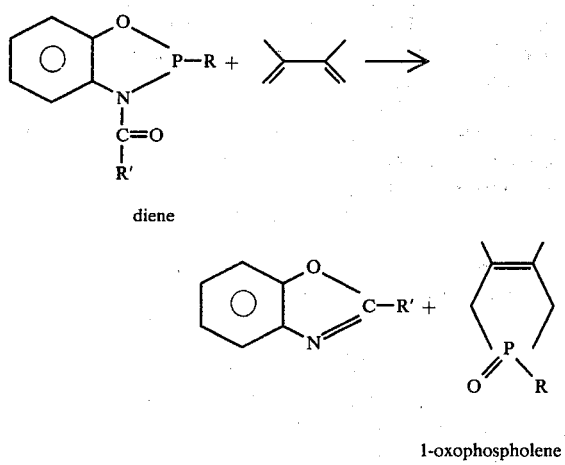

Alkyl- and aryl-1-oxophospholenes, can be used, inter alia, as catalysts for the manufacture of high quality and economically important rigid polyurethane foams for technical purposes (cf. for example DE-OS No. 2,606,682, DE-AS No. 2,036,173 and US-PS No. 3,855,186).

So far, only two defined 3-acyl-2-alkyl- and 3-acyl-2-aryl-1,3,2-benzoxazaphospholanes have become known, i.e. 3-acetyl-2-ethyl- and 3-acetyl-2-phenyl-1,3,2-benzoxazaphospholane (cf. M. and A. Pudovik et al., Zh.Obsh.Khim. 44, 1020, (1974)). They are prepared from ethyl- or phenyldichlorophosphane, 2-N-acetylaminophenol and organic nitrogen bases binding hydrogen chloride (in an inert solvent) in a two stage reaction. In the first stage the respective phosphonous acid diamide is prepared and isolated from dichlorophosphane and diethylamine and in the second stage the compound obtained is reacted with 2-N-acetylaminophenol to give the corresponding benzoxazaphospholane. The two stages of the reaction can be illustrated by the following equations

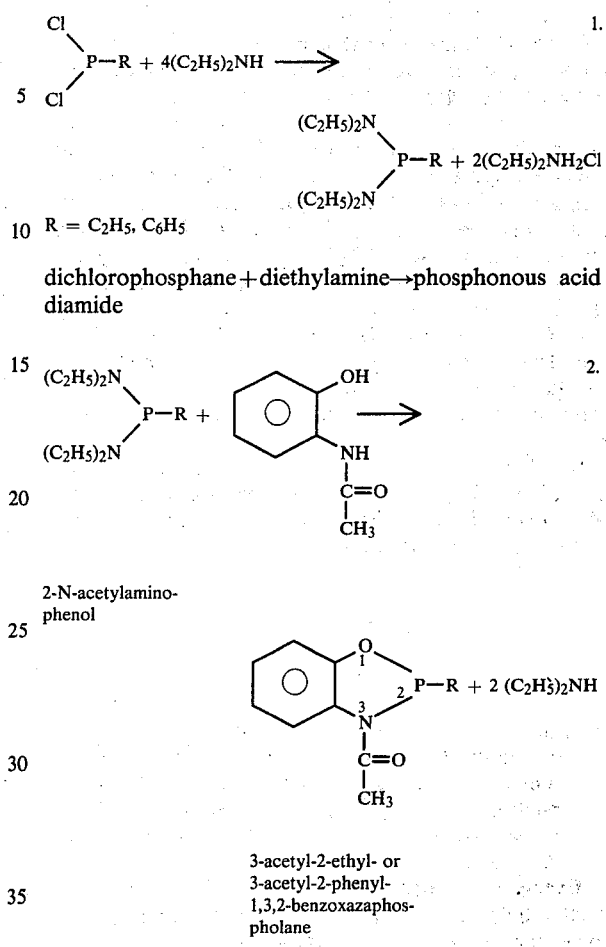

$R = C_2H_5, C_6H_5$ dichlorophosphane + diethylamine → phosphonous acid diamide 2-N-acetylaminophenol 3-acetyl-2-ethyl- or 3-acetyl-2-phenyl-1,3,2-benzoxazaphospholane This two-stage process for the manufacture of benzoxazaphospholanes is too complicated and uneconomic for being carried out on an industrial scale, especially since the yield in the essential second stage amounts to only about 55 to 64% of the theoretical.

It has, therefore, been desirable to develop a more simple and economic improved process which can be used not only for the manufacture of the known 3-acetyl-2-ethyl- and 3-acetyl-2-phenyl-1,3,2-benzoxazaphospholane, but also for the manufacture of other novel benzoxazaphospholanes.

According to the invention this could be achieved by reacting dichlorophosphanes with 2-N-acylaminophenols in the presence of organic nitrogen bases binding hydrogen chloride in an inert solvent in a one stage process without isolation of an intermediate product.

It is the object of the invention to provide a process for the manufacture of 3-acyl-2-alkyl- and 3-acyl-2-aryl-1,3,2-benzoxazaphospholanes from dichlorophosphanes, N-acylaminophenols and organic nitrogen bases binding hydrogen chloride, in an inert solvent, which comprises reacting dichlorophosphanes, 2-N-acylaminophenols and organic nitrogen bases binding hydrogen chloride in a molar proportion of about $1:1 \geq 2$ in a one stage process in an inert solvent without isolation of an intermediate product.

It was extremely surprising that the reaction could be carried out without isolation of an intermediate and in one stage as normally carboxylic acid amides such as 2-N-acylaminophenols can be acylated (for a second time) at the nitrogen atom under severe conditions only by an acid chloride.

It was also surprising that in the one stage process according to the invention very high and even almost quantitative yields of the desired benzoxazaphospholanes are obtained, in view of the considerably lower yields of the two stage process of the state of the art. In the one stage process according to the invention the reaction of phenyldichlorophosphane with 2-N-acetylaminophenol and triethylamine, for example, gives a yield of 3-acetyl-2-phenyl-1,3,2-benzoxazaphospholane of 99.6%, whereas the same compound is obtained in a yield of only 52% of the theory by reacting phosphonous acid bis-diethylamide with 2-N-acetylaminophenol. The comparison of the yields would be still more favorable is the yield of the first stage of the process of the state of the art is also considered.

Suitable dichlorophosphanes in the process of the invention are, in principle, all possible organo-dichlorophosphanes. It is preferred, however, to use dichlorophosphanes of the formula I

in which
R$_2$ denotes (C$_1$–C$_{12}$)alkyl, preferably (C$_1$–C$_4$)alkyl which may be substituted by Cl and/or Br; cyclopentyl, cyclohexyl, phenyl or naphthyl which may be substituted by Cl, Br, (C$_1$–C$_4$)alkyl and/or (C$_1$–C$_4$)alkoxy.

Examples of dichlorophosphanes of formula I are methyldichlorophosphane, ethyldichlorophosphane, butyldichlorophosphane, chloromethyldichlorophosphane, phenyldichlorophosphane, naphthyldichlorophosphane. They can be obtained by known processes (cf. K. Sasse in Houben-Weyl, Methoden der organischen Chemie, edited by G. Thieme, Stuttgart 1963, volume 12/1, pages 302 et seq.). Especially preferred phosphanes are methyldichlorophosphane, ethyldichlorophosphane and phenyldichlorophosphane.

Suitable 2-N-acylaminophenols are, in principle, all compounds having the basic 2-N-acylaminophenol skeleton, preferably, however, compounds of the formula II

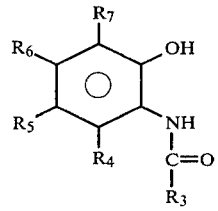

in which
R$_3$ denotes hydrogen, (C$_1$–C$_{12}$)alkyl, preferably (C$_1$–C$_4$)alkyl, which may be substituted by Cl and/or Br; cyclopentyl, cyclohexyl, phenyl or naphthyl which may be substituted by Cl, Br, (C$_1$–C$_4$)alkyl and/or (C$_1$–C$_4$)alkoxy, and
R$_4$–R$_7$, independent of one another, denote hydrogen, (C$_1$–C$_4$)alkyl, (C$_1$–C$_4$)alkoxy, Cl or Br.

Suitable N-acylaminophenols of formula II are, for example, 2-N-acetylaminophenol, 2-N-propionylaminophenol, 2-N-butanoylaminophenol, 2-N-benzoylaminophenol, 2-N-acetylamino-3-chlorophenol, 2-N-acetylamino-4-chlorophenol, 2-N-acetylamino-5-chlorophenol, 2-N-acetylamino-6-chlorophenol, or the corresponding bromine derivatives, 3-N-acetamino-4-oxytoluene, 4-N-acetylamino-3-oxytoluene, 5-N-acetylamino-4-oxy-1,2-xylene, 2-N-acetamino-4-methoxyphenol and the like. The N-acylaminophenols are prepared according to known methods by acylation of the respective carboxylic acid anhydrides and the free anilines (cf. for example, Fierz-David and Kuster, Helv.Chim.Acta 22, 82 (1939) or L. R. Raiford and C. Greider, J.Am.Chem.Soc. 46, 432 (1924)).

Organic nitrogen bases to be used as hydrogen chloride binding agent are, above all, primary, secondary and tertiary amines, preferably those having from 1 to 12 carbon atoms in the molecule, for example triethylamine, N,N-dimethylaniline, pyridine, diethylamine, dimethylamine, N-methylaniline, piperidine, dicyclohexylamine, methylamine, ethylamine, propylamine, butylamine, cyclohexylamine and aniline.

Suitable solvents that are inert towards the starting compounds and final products are aliphatic and aromatic hydrocarbons, preferably those having from 5 to 8 carbon atoms, for example heptane, hexane, pentane, gasoline mixtures having from 5 to 8 carbon atoms, xylene, toluene, or benzene; chlorinated hydrocarbons such as methylene chloride, chloroform or carbon tetrachloride as well as di- and trichloroethane; and inert ethers, for example tetrahydrofurane, dioxane, diisopropyl ether and diethyl ether.

The process according to the invention can be carried out in a relatively broad temperature range. In general, the temperature ranges from about −50° to +150° C., preferably from about +20° to +90° C. The reaction time is from a few minutes to a few hours, preferably about 30 to 60 minutes.

The process is preferably carried out in an inert gas atmosphere such as nitrogen, carbon dioxide or argon.

The proportion of solvent to the sum of all reactants can be varied within a relatively wide range. In general, a proportion by weight of about 2:1 to about 10:1 (solvent:sum of reactants), preferably of about 3:1 to about 6:1 and more preferably of about 4:1 is chosen.

In general, the reactants are first mixed and the mixture is heated or one of the reactants, preferably the dichlorophosphane, is added dropwise to the solution or suspension of the 2-N-acylaminophenol in the solvent/base mixture. The reaction heat is generally utilized for heating the reaction mixture without external cooling, whereby the after-heating time to complete the reaction is shortened.

It proved advantageous to use the organodichlorphosphane and the 2-N-acylaminophenol in a molar proportion of approximately 1:1. The nitrogen base binding hydrogen chloride is generally used in an amount of approximately 2 mols for each mol of dichlorophosphane, it can, however, also be used in an excess.

For working up the reaction mixture, the hydrochloride precipitate is separated by filtration with or without pressure or by centrifugation.

After separation of the precipitated salt, the solution containing the reaction product is freed from solvent by distillation at atmospheric pressure or reduced pressure. After removal of the solvent under reduced pressure, the 3-N-acyl-2-alkyl(aryl)-1,3,2-benzoxazaphospholane separates mostly in the form of pure crystals. Normally, a further purification of the reaction products is unnecessary. If desired, however, they can be further purified by known methods, for example by distillation under reduced pressure or recrystallization.

The benzoxazaphospholanes obtainable by the process according to the invention have the formula

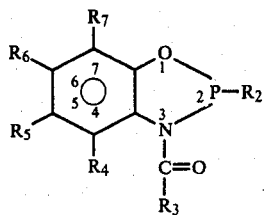

(III)

in which $R_2$ to $R_7$ are as defined under formulae I and II, and are novel with the exception of those compounds in which $R_2$ is $C_2H_5$ or $C_6H_5$, $R_3$ is $CH_3$ and $R_4$ to $R_7$ are hydrogen.

Preferred 3-acyl-2-alkyl- and 3-acyl-2-aryl-1,3,2-benzoxazaphospholanes are compounds of formula III in which $R_2$ denotes $CH_3$ or $C_6H_5$, $R_3$ denotes hydrogen or $(C_1-C_4)$alkyl and $R_4$ to $R_7$, independent of one another, are hydrogen, $CH_3$ or Cl, with the exception that $R_2$ is not $C_6H_5$, $R_3$ is not $CH_3$ and $R_4$ to $R_7$ are not hydrogen.

The novel compounds are used for the same purposes as the known compounds of this class.

The following Examples illustrate the invention.

EXAMPLE 1

200 ml (2.2 mols) of methyldichlorophosphane are added dropwise within 10 minutes and under $N_2$ to a suspension of 332 g (2.2 mols) of 2-N-acetylaminophenol in 4 l of toluene and 460 g (4.55 mols) of triethylamine. The temperature of the reaction solution automatically rises to about 50° C. When the addition is terminated, the mixture is heated for 30 minutes to 90° C. and cooled, whereupon the precipitated triethylamine-hydrochloride is filtered off under nitrogen in a pressure filtering flask. The filtrate is concentrated by evaporation at 40° C. and 12 torr, adhering solvent residues are removed at 30° C. and 0.1 torr and crystallization is started by rubbing. 424 g (98.8% of theory) of 3-acetyl-2-methyl-1,3,2-benzoxazaphospholane melting at 43°–46° C. are obtained.

Calculated C 55.39%; H 5.16%; N 7.18%; P 15.87%; found C 55.10%; H 5.30%; N 7.40%; P 15.80%.

$C_9H_{10}NO_2P$ (195.2)

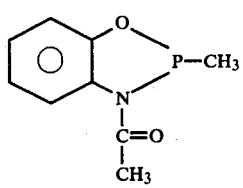

EXAMPLE 2

In the manner described in Example 1, 332 g (2.2 mols) of 2-N-acetylaminophenol are reacted with 394 g (2.2 mols) of phenyldichlorophosphane and 460 g (4.55 mols) of triethylamine in toluene and the mixture is worked up. 563 g (99.6% of theory of 3-acetyl-2-phenyl-1,3,2-benzoxazaphospholane melting at 73°–75° C. are obtained.

Calculated C 65.37%; H 4.70%; N 5.45%; P 12.04%; found C 64.70%; H 4.80%; N 5.50%; P 11.70%.

$C_{14}H_{12}NO_2P$ (257.2)

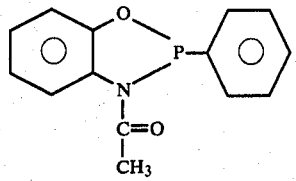

COMPARATIVE EXAMPLE 2

200.0 g (0.79 mol) of phenylphosphonous acid bis-diethylamide are rapidly added dropwise and under $N_2$ to 119.3 g (0.79 mol) of N-acetylaminophenol in 1,000 ml of toluene. The mixture is refluxed until no more diethylamine escapes (6 hrs) and the solvent is removed at 50° C. at 15 torr. The resinous residue is taken up in 300 ml of ether, rubbed for crystallization and kept for 1 hr at 0° C. Suction filtration yields 106.0 g (52% of theory) of 3-acetyl-2-phenyl-1,3,2-benzoxazaphospholane melting at 73°–74° C.

EXAMPLE 3

50 ml (0.55 mol) of methyldichlorophosphane are added dropwise within 10 minutes and under $N_2$ to a suspension of 98.5 g (0.55 mol) of 5-N-acetylamino-4-hydroxy-1,2-xylene in 1 liter of toluene and 115 g (1.14 mols) of triethylamine. When the addition is terminated, the mixture is kept for 15 minutes at 90° C., cooled and the precipitated triethylamine hydrochloride is filtered off with suction. The filtrate is concentrated by evaporation at 40° C. and 12 torr, adhering solvent residues are removed at 30° C. under 0.1 torr and the remainder is rubbed to start crystallization. 119 g (97.1% of theory) of 3-acetyl-2-methyl-5,6-dimethyl-1,3,2-benzoxazaphospholane melting at 102° to 103° C. are obtained.

Calculated C 59.19%; H 6.32%; N 6.28%; P 13.88%; found C 60.50%; H 6.70%; N 6.20%; P 13.30%.

$C_{11}H_{14}NO_2P$ (223.2)

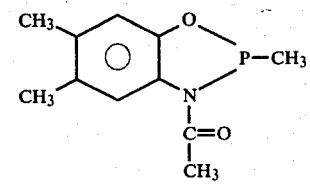

EXAMPLE 4

In the manner described in Example 3, 98.5 g (0.55 mol) of 5-N-acetylamino-4-hydroxy-1,2-xylene are reacted with 98.5 g (0.55 mol) of phenyldichlorophosphane and 115 g (1.14 mols) of triethylamine in toluene and the reaction mixture is worked up. 153 g (97.5% of the theory) of 3-acetyl-2-phenyl-5,6-dimethyl-1,3-2-benzoxazaphospholane melting at 73° C. are obtained.

Calculated C 67.36%; H 5.65%; N 4.91%; P 10.86%; Found C 67.40%; H 5.80%; N 5.10%; P 10.60%.

$C_{16}H_{16}NO_2P$ (285.3) 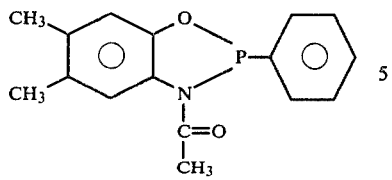

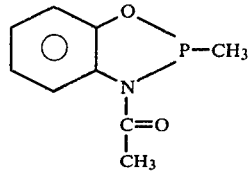

EXAMPLE 5

In the manner described in Example 3, 102.0 g (0.55 mol) of 2-N-acetylamino-4-chlorophenol are reacted with 50 ml (0.55 mol) of methyldichlorophosphane and 115 g (1.14 mols) of triethylamine in toluene and the reaction mixture is worked up. 125 g (98.9% of theory) of 3-acetyl-2-methyl-5-chloro-1,3,2-benzoxazaphospholane melting at 49°–51° C. are obtained.

Calculated C 47.08%; H 3.95%; N 6.10%; P 13.49%; Found C 47.00%; H 4.20%; N 6.30%; P 13.10%.

$C_9H_9ClNO_2P$ (229.6) 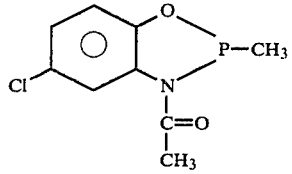

EXAMPLE 6

In the manner described in Example 5, 102.0 g (0.55 mol) of 2-N-acetylamino-4-chlorophenol are reacted with 98.5 g (0.55 mol) of phenyldichlorophosphane and 115 g (1.14 mols) of triethylamine in toluene and the reaction mixture is worked up. 154 g (96% of theory) of 3-acetyl-2-phenyl-5-chloro-1,3,2-benzoxazaphospholane melting at 56°–58° C. are obtained.

Calculated C 57.65%; H 3.80%; N 4.80%; P 10.62%; found C 57.60%; H 4.00%; N 4.90%; P 10.30%.

$C_{14}H_{11}ClNO_2P$ (291.7) 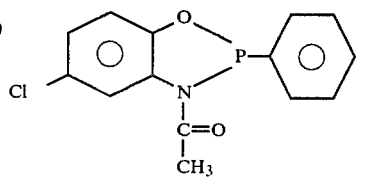

EXAMPLE 7

36 g (0.16 mol) of methylamine are introduced at 0° C. into a suspension of 83.7 g (0.55 mol) of 2-N-acetylaminophenol in 1 l of toluene. 50 ml (0.55 mol) of methyldichlorophosphane are then added dropwise under $N_2$ and at 0° C. with external cooling. The mixture is kept for 1 hr at 100° C., cooled and filtered with suction. After removal of the solvent at 40° C. and under 12 torr, 105 g (97.9% of the theory) of 3-acetyl-2-methyl-1,3,2-benzoxazaphospholane are obtained from the filtrate.

EXAMPLE 8

20 ml (0.22 mol) of methyldichlorophosphane are added dropwise and under $N_2$ to a solution of 36.3 g (0.22 mol) of 2-N-propionylaminophenol in 500 ml of toluene and 46 g (0.45 mol) of triethylamine. When the addition is terminated, the mixture is kept for 15 minutes at 90° C. and the precipitated triethylamine hydrochloride is filtered off with suction. The filtrate is concentrated by evaporation at 40° C. under 12 torr and adhering solvent residues are removed at 30° C. under 0.1 torr. 45.6 g (99% of theory) of 3-propionyl-2-methyl-1,3,2-benzoxazaphospholane are obtained in the form of a colorless oil.

Calculated C 57.42%; H 5.78%; N 6.70%; P 14.81%; found C 57.40%; H 5.70%; N 6.80%; P 13.60%.

$C_{10}H_{12}NO_2P$ (209.2) 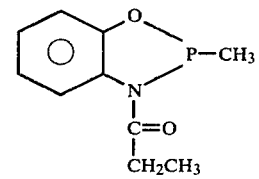

EXAMPLE 9

In the manner described in Example 8, 151 g (1.1 mols) of 2-N-formylaminophenol are reacted with 100 ml (1.1 mols) of methyldichlorophosphane and 230 g (2.28 mols) of triethylamine in toluene and the reaction mixture is worked up. 195.5 g (98.2% of theory) of 3-formyl-2-methyl-1,3,2-benzoxazaphospholane are obtained in the form of a light yellow oil.

Calculated C 53.5 H 4.45 N 7.73 P 17.1; found C 52.2 H 4.3 N 7.8 P 16.1.

$C_8H_8NO_2P$ (181.1) 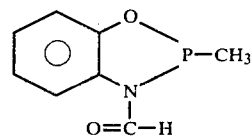

EXAMPLE 10

In the manner described in Example 8, 151 g (1.1 mols) of 2-N-formylaminophenol are reacted with 148 ml (1.1 mols) of phenyldichlorophosphane and 230 g (2.28 mols) of triethylamine in toluene and the reaction mixture is worked up. 259 g (97% of theory) of 3-formyl-2-phenyl-1,3,2-benzoxazaphospholane are obtained in the form of a light yellow oil.

Calculated C 64.20 H 4.14 N 5.76 P 12.74; found C 63.9 H 4.4 N 6.0 P 11.5.

$C_{13}H_{10}NO_2P$ (243.2)

What is claimed is:

1. Process for the manufacture of 3-acyl-2-alkyl- and 3-acyl-2-aryl-1,3,2-benzoxazaphospholanes which comprises reacting dichlorophosphanes, 2-N-acylaminophenols and organic nitrogen bases binding hydrogen chloride in a molar proportion of about $1:1:\geqq 2$ in a one stage process and in an inert solvent without isolation of an intermediate product.

2. The process claimed in claim 1, wherein the dichlorophosphanes have the formula:

[(I)]

in which $R_2$ denotes $(C_1-C_{12})$alkyl, cyclopentyl, cyclohexyl, phenyl or naphthyl which may be substituted by Cl, Br, $(C_1-C_4)$ alkyl and/or $(C_1-C_4)$alkoxy are used.

3. The process of claim 1, wherein the 2-N-acylaminophenols have the formula

[(II)]

in which $R_3$ denotes hydrogen, $(C_1-C_{12})$alkyl, cyclopentyl, cyclohexyl, phenyl or naphthyl which may be substituted by Cl, Br, $(C_1-C_4)$alkyl and/or $(C_1-C_4)$alkoxy, and $R_4-R_7$, independent of one another, denote hydrogen, $(C_1-C_4)$alkyl, $(C_1-C_4)$alkoxy, Cl or Br are used.

4. Process as claimed in claim 1, wherein primary, secondary and/or tertiary amines having from 1 to 12 carbon atoms in the molecule are used as organic nitrogen bases binding hydrogen chloride.

5. Process as claimed in claim 1, wherein aliphatic and/or aromatic hydrocarbons having from 5 to 8 carbon atoms, chlorohydrocarbons having 1 or 2 carbon atoms and/or aliphatic ethers having from 4 to 6 carbon atoms are used as solvent.

6. Process as claimed in claim 1, wherein the reaction is carried out at a temperature of from about $-50°$ to $+150°$ C.

7. The process of claim 2 wherein $R_2$ is an alkyl group having from 1 to 4 carbon atoms which may be substituted by either Cl or Br or both.

8. The process of claim 3 wherein $R_3$ is an alkyl group having from 1 to 4 carbon atoms which may be substituted by Cl or Br or both.

9. The process of claim 6 wherein the reaction is carried out at a temperature of from about 20° to 90° C.

* * * * *